United States Patent [19]

Heise et al.

[11] 4,404,400
[45] Sep. 13, 1983

[54] PROCESS FOR THE PREPARATION OF 4-NITRODIPHENYLAMINES

[75] Inventors: Klaus-Peter Heise, Bergisch Gladbach; Karlfried Wedemeyer, Cologne, both of Fed. Rep. of Germany

[73] Assignee: Bayer Aktiengesellschaft, Leverkusen, Fed. Rep. of Germany

[21] Appl. No.: 414,224

[22] Filed: Sep. 2, 1982

[30] Foreign Application Priority Data

Sep. 17, 1981 [DE] Fed. Rep. of Germany ....... 3137041

[51] Int. Cl.³ ............................................ C07C 85/04
[52] U.S. Cl. .................................................. 564/406
[58] Field of Search ........................................ 564/406

[56] References Cited

U.S. PATENT DOCUMENTS 3,313,854  4/1967  Levy ................................. 564/406
3,393,241  7/1968  Nielsen ............................. 564/406
4,122,118  10/1978 George et al. ..................... 564/406

Primary Examiner—Paul F. Shaver
Attorney, Agent, or Firm—Sprung, Horn, Kramer & Woods

[57] ABSTRACT

The invention relates to a process for the preparation of 4-nitrodiphenylamines by the reaction of halogenonitrobenzenes with primary aromatic amines in the presence of copper or a copper compound, a neutralizing agent and a cyclic diaza compound.

12 Claims, No Drawings

PROCESS FOR THE PREPARATION OF 4-NITRODIPHENYLAMINES

The invention relates to a process for the preparation of 4-nitrodiphenylamines by the reaction of halogenonitrobenzenes with primary aromatic amines in the presence of copper or copper compounds and in the presence of a neutralizing agent.

The reaction of halogenonitrobenzenes with aromatic amines has already been known for a long time. Thus, German Pat. No. 185,663, British Pat. No. 24,091 and French Pat. No. 381,230 disclose that the reaction is carried out in the presence of alkali metal carbonates and copper compounds as catalysts.

In addition, it is known that the extraordinarily slow reaction can be accelerated if potassium carbonate is employed and the water of reaction is removed by azeotropic distillation. According to Example 1 of U.S. Pat. No. 2,927,943, moderately pure 4-nitrodiphenylamine was obtained under these conditions in a reaction time of 21 hours, in a yield of 73% of theory. Furthermore, U.S. Pat. No. 4,155,936 discloses that in the reaction of halogenonitrobenzenes with primary aromatic amines, apart from the disadvantage of longer reaction times, the nitrodiphenylamines are contaminated as a result of the formation of substantial amounts of tars and by-products, such as the formation of nitrobenzene as a result of reductive dehalogenation (see U.S. Pat. No. 3,313,854, column 3, lines 64, 65).

To avoid these disadvantages, polar solvents were added to the reaction mixture, as co-catalysts. However, the polar solvents hitherto employed, without exception, are also associated with disadvantages. Thus, dimethylformamide, which is employed according to U.S. Pat. No. 3,055,940, is volatile under the reaction conditions, and forms by-products which are difficult to separate off. Hexamethylphosphoric acid triamide, which is employed according to U.S. Pat. No. 3,055,940, and formanilide, which is employed according to U.S. Pat. No. 3,313,854, possess only unsatisfactory accelerating properties in catalytic amounts in the presence of copper compounds. Dimethylsulphoxide, acetanilide and salicylanilide, which are employed according to U.S. Pat. No. 3,277,175, German Auslegeschrift No. 1,518,307 and German Auslegeschrift No. 1,117,594, also produce only slight effects. When the polar solvents mentioned are employed, and also when N-methylpyrrolidone is employed according to German Offenlegungsschrift No. 2,633,811 or ε-caprolactam according to J 56022-751 (1981), the processes are, in addition, either restricted from the outset to the use of potassium carbonate as the neutralizing agent, or, when sodium carbonate (see German Auslegeschrift No. 1,117,594, Examples 14 and 15) or other neutralizing agents (see German Auslegeschrift No. 1,518,307, column 3, lines 31–34) are used, appreciably poorer yields and purities of 4-nitrodiphenylamines are achieved.

The addition of polyethers, which is described in U.S. Pat. No. 4,155,936, is also associated with disadvantages. Depending on the method of working-up, the additives, in fact, remain in the end product or in the waste water. In addition, contact with polyethers is unacceptable toxicologically.

As a further possibility of reducing the production of tar, U.S. Pat. No. 3,121,736 describes the addition of aminocarboxylic acids, such as glutamic acid or phenylalanine, of alkyldiaminopolycarboxylic acids and their salts, preferably tetrasodium ethylenediaminetetraacetate, of disalicylaldiaminoalkanes, preferably 1,2-disalicylaldiaminopropane, of o-hydroxybenzalaminophenols, preferably o-hydroxybenzal-o-aminophenol, of polyphosphates, carboxymethyl-mercaptosuccinic acid or Schiff's bases of salicylaldehydes. In the examples mentioned in U.S. Pat. No. 3,121,736, potassium carbonate, which is expensive, is exclusively used as the neutralizing agent. In addition, as is evident from a comparison of Examples 1 and 2, the tetrasodium ethylenediaminetetraacetate added has an inhibiting effect on the conversion of the halogenoaromatic compound, and this results in additional problems in the working-up. In addition, experiments of the applicant using the additives mentioned in U.S. Pat. No. 3,121,736 have shown that the additives, in the presence of sodium carbonate as the neutralizing agent, either have an inhibiting effect on the formation of nitrodiphenylamine, or promote side-reactions, such as the formation of nitrobenzene, to a very great extent.

A process for the preparation of 4-nitrodiphenylamines of the formula (I)

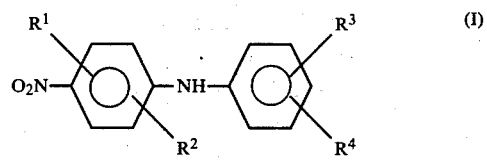

in which
R$^1$, R$^2$, R$^3$ and R$^4$ are identical or different and represent hydrogen or an alkyl radical having 1 to 9 carbon atoms,
by the reaction of halogenonitrobenzenes of the formula (II)

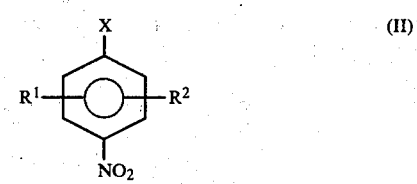

in which
X represents chlorine or bromine and
R$^1$ and R$^2$ have the abovementioned meaning,
with primary aromatic amines of the formula (III)

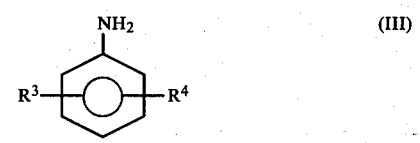

in which R$^3$ and R$^4$ have the abovementioned meaning, in the presence of a neutralizing agent and in the presence of copper or copper salts has now been found, which is characterized in that the reaction is carried out in the presence of a cyclic 1,n-diaza compound wherein n=3, 4 or 5, wherein the nitrogen atoms do not carry any hydrogen and at least one nitrogen atom is a constituent of a double bond and at least one nitrogen atom is a constituent of a ring, and the 1,n-diaza compound is not capable of forming an anion in an aqueous-alkaline solution.

Suitable alkyl radicals of the formula (I) are those having 1 to 9, preferably 1 to 3, carbon atoms. The following may be mentioned: the methyl, ethyl, n-propyl, iso-propyl, n-butyl, iso-butyl, tert.-butyl, n-pentyl, iso-pentyl, n-hexyl, n-heptyl, n-octyl and n-nonyl radical, preferably the methyl, ethyl, n-propyl and iso-propyl radical.

Imidazoles or imidazolines of the formulae (IV) to (VI)

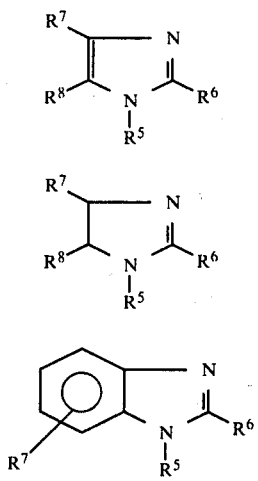

in which
R$^5$ denotes alkyl, aryl or aralkyl, and
R$^6$, R$^7$ and R$^8$ represent hydrogen, alkyl, aryl or aralkyl, can be employed as cyclic, 1,n-diaza compounds in the process according to the invention.

The following are examples of imidazole derivatives which can be employed: 1-methyl-1-H-imidazole, 1-ethyl-1-imidazole, 1-butyl-1-H-imidazole, 1-phenyl-1-H-imidazole, 1-benzyl-1-H-imidazole, 1,2-dimethyl-1-H-imidazole, 1,2,4,5-tetramethyl-1-H-imidazole, 1-methylbenzimidazole, 1-ethyl-2-methyl-benzimidazole, 1-butyl-4,5-dihydro-1-H-imidazole or 1-benzyl-2-methyl-4,5-dihydro-1-H-imidazole, preferably 1-methyl-1-H-imidazole and 1,2-dimethyl-1-H-imidazole.

Furthermore, pyrimidines of the formula (VII)

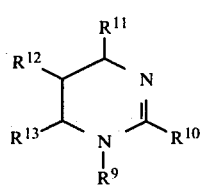

wherein
R$^9$ represents alkyl, aryl or aralkyl, and
R$^{10}$, R$^{11}$, R$^{12}$ and R$^{13}$ independently of one another denote hydrogen, alkyl, aryl or aralkyl, or cyclic amidines of the formula (VIII)

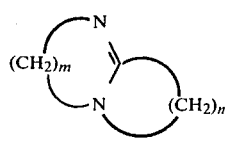

wherein
n=3, 4 or 5 and
m=2, 3 or 4,
or triazines of the formula (IX)

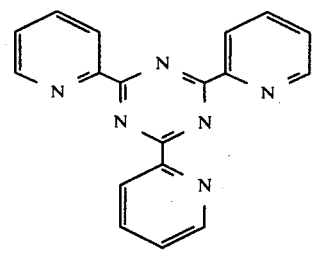

or phenanthrolines of the formula (X)

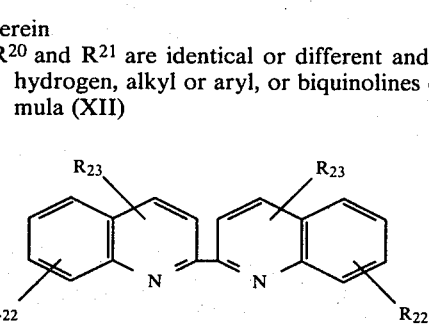

wherein
R$^{14}$, R$^{15}$, R$^{16}$, R$^{17}$, R$^{18}$ and R$^{19}$ are identical or different and represent hydrogen, alkyl or aryl, or dipyridines of the formula (XI)

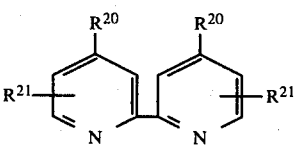

wherein
R$^{20}$ and R$^{21}$ are identical or different and represent hydrogen, alkyl or aryl, or biquinolines of the formula (XII)

wherein
R$^{22}$ and R$^{23}$ are identical or different and represent hydrogen, alkyl or aryl, can be employed as 1,n-diaza compounds in the process according to the invention.

Suitable alkyl radicals of the formulae (IV) to (VII), (X) and (XI) are those having 1 to 9, preferably 1 to 3, carbon atoms. The following may be mentioned: the methyl, ethyl, n-propyl, iso-propyl, n-butyl, isobutyl, tert.-butyl, n-pentyl, iso-pentyl, cyclo-pentyl, n-hexyl, cyclo-hexyl, n-heptyl, n-octyl and n-nonyl radicals, preferably the methyl, ethyl and iso-propyl radicals.

Suitable aryl radicals of the formulae (IV) to (VII) and (X) to (XII) are those having 6 to 14, preferably 6 to 8, carbon atoms. The following may be mentioned: the phenyl, tolyl, xylyl and naphthyl radicals, preferably the phenyl radical.

Suitable aralkyl radicals of the formulae (IV) to (VII) are those having 1 to 6, preferably 1 to 2, carbon atoms in the aliphatic part and 6 to 14, preferably 6, carbon atoms in the aromatic part. The following may be mentioned: the benzyl radical and the ethylphenyl radical, preferably the benzyl radical.

For example, 1-methyl-1,4,5,6-tetrahydropyrimidine, 1,2-dimethyl-1,4,5,6-tetrahydropyrimidine or 1-ethyl-1,4,5,6-tetrahydropyrimidine, preferably 1,2-dimethyl-1,4,5,6-tetrahydropyrimidine, can be employed as pyrimidine derivatives, 1,5-diaza-bicyclo[4,3,0]non-5-ene, 1,5-diaza-bicyclo[4,4,0]dec-5-ene, 1,6-diaza-bicyclo[5,3,0]dec-6-ene or 1,8-diaza-bicyclo[5,4,0]undec-7-ene, preferably 1,8-diaza-bicyclo[5,4,0]undec-7-ene, can be employed as bicyclic amidines, 2,4,6-tri-(pyrid-2-yl)-1,3,5-triazine can be employed as a triazine derivative, 1,10-phenanthroline, 2,9-dimethyl-1,10-phenanthroline, 2,9-dimethyl-4,7-diphenyl-1,10-phenanthroline, 4,7-diphenyl-1,10-phenanthroline or 4,7-dimethyl-1,10-phenanthroline, preferably 1,10-phenanthroline and 2,9-dimethyl-1,10-phenanthroline, can be employed as phenanthrolines, 2,2'-bipyridine, 4,4'-dimethyl-2,2'-bipyridine, 4,4'-diethyl-2,2'-bipyridine, 4,4',6,6'-tetramethyl-2,2'-bipyridine or biquinoline, preferably 2,2'-bipyridine and biquinoline, can be employed as bipyridines, and 4-dimethylaminopyridine or 4-pyrrolidinoamino-pyridine, preferably 4-dimethylaminopyridine, can be employed as aminopyridines.

The 1,n-diaza compounds can, of course, also be employed in the form of their salts, for example as hydrochlorides, or mixed with one another. The 1,n-diaza compounds according to the invention are commercially available substances or can be prepared according to processes known from the literature. The amount of 1,n-diaza compounds employed can vary within wide limits. In general, about 0.1 to 10% by weight, preferably 0.5 to 5% by weight, of 1,n-diaza compounds, relative to halogenonitrobenzene used, is employed.

Copper powder, copper(I)iodide, copper(I)chloride, copper(II)chloride, copper(I)bromide, copper(II)bromide, copper(I)cyanide, copper(I)oxide, copper(II)oxide, copper(II)carbonate, basic copper(II)carbonate, copper(II)sulphate, copper(II)nitrate, copper(II)formate or copper(II)acetate may be mentioned as examples of copper catalysts which can be used in the process according to the invention. Copper salts of weak acids, such as copper(II)oxide, copper(II)carbonate, basic copper(II)carbonate or copper(I)cyanide, are preferably employed, the copper catalyst being employed in an amount of at least 0.1% by weight, preferably from 0.3 to 2% by weight, relative to halogenonitrobenzene used. The copper catalysts can be employed both individually and mixed with one another. They can also be employed in the form of complex compounds of copper and 1,n-diaza compounds.

The weight ratio, of the copper catalyst to the 1,n-diaza compound, which is most favourable for the particular reaction can readily be determined by simple experiments.

Halogenonitrobenzenes suitable for the process according to the invention are compounds of the formula (II)

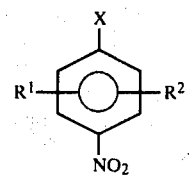

in which
X represents chlorine or bromine, and
R¹ and R² have the meaning mentioned for formula (I).

For example, the following compounds of the formula (II) can be employed: 4-nitrochlorobenzene, 4-nitrobromobenzene, 4-nitro-2-methylchlorobenzene and 4-nitro-3-methylchlorobenzene.

Compounds of the formula (III)

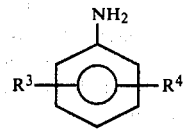

in which
R³ and R⁴ have the meaning mentioned for formula (I), can be employed as primary aromatic amines in the process according to the invention.

For example, the following primary aromatic amines of the formula (III) can be employed: aniline, o-toluidine, m-toluidine, p-toluidine, 4-ethylaniline, 4-butylaniline, 4-isopropylaniline, 3,5-dimethylaniline and 2,4-dimethylaniline.

The aromatic amines can, of course, also be employed in the form of mixtures, in particular isomer mixtures. In general about 1 to 6 mols, preferably 1.5 to 3 mols, particularly 1.7 to 2.5 mols, of the aromatic amine are employed per mole of the halogenonitrobenzene.

Alkali metal hydroxides, alkali metal salts and oxides of alkali metals can be employed as neutralizing agents in the process according to the invention. Alkali metal carbonates, in particular potassium carbonate and/or sodium carbonate, are preferably employed. The neutralizing agent can be employed in an equivalent amount or in excess, preferably in 1.05 to 1.5 times the equivalent amount.

By using the 1,n-diaza compounds according to the invention, very good yields of 4-nitrodiphenylamines are obtained even when sodium carbonate is employed, and this results in economic and ecological advantages—no pollution of the waste water with potassium ions. The neutralizing agent is advantageously used in an anhydrous and finely divided form. For example, calcined sodium carbonate of the "light" type is suitable for the process according to the invention.

The reactants are reacted as far as possible under anhydrous conditions. If neutralizing agents which form water during the reaction are used, the water of reaction is advantageously removed from the reaction mixture by distillation, with the aid of an entraining agent. Examples of suitable entraining agents are the following compounds: xylene, toluene, benzene, chlorobenzene, chlorotoluene, aniline and/or toluidine.

If desired, the process according to the invention can be carried out in the presence of diluents, for example inert organic hydrocarbons, for example in the presence of xylene. Furthermore, the aromatic primary amines themselves can be employed as solvents.

The reaction temperatures of the process according to the invention can vary within wide ranges. In general they are about 150° to 225° C., preferably 185° to 205° C.

The process according to the invention can be carried out continuously or discontinuously, according to customary methods. For example, in the case of a discontinuous procedure, the components can be introduced into a reactor provided with a stirrer, and heated to the reaction temperature. On the other hand, the copper compound can be brought into contact with the 1,n-diaza compound according to the invention, if appropriate in the presence of the compounds of the formula (II) and/or (III) and/or the entraining agent, preferably at a temperature of from 100° to 160° C., for example even in a phase upstream from the actual reaction. The last-mentioned variant is preferably used.

Water formed in the reaction is advantageously removed from the reaction mixture by distillation, if necessary with the aid of the additional entraining agent. The reaction is terminated when the desired degree of conversion of the halogenonitrobenzene is reached. The reaction is preferably terminated when a degree of conversion of at least 96% has been reached.

The reaction mixture can also be worked up according to various variants. In the presence of the 1,n-diaza compounds according to the invention, the formation of tar is suppressed to such an extent that it is possible to separate off the salts present in the reaction mixture without problems, at elevated temperature, in a physical manner by centrifuging or filtering. After washing with warm xylene and drying, a pale grey pulverulent solid remains. Unreacted halogenonitrobenzene and the primary aromatic amine can be expelled from the filtrate with stream, and the nitrodiphenylamines are mostly produced in the form of granules. Another possibility consists in subjecting the filtrate to incipient distillation in vacuo and then obtaining the product in the residue, or in substantially separating off the 4-nitrodiphenylamines by crystallization, and/or in adding a precipitating agent, for example xylene, to the filtrate. In this procedure, the 4-nitrodiphenyls are produced in a highly pure form and can thus be directly processed further.

In most cases, the mother liquor can be recycled without it being necessary to employ fresh copper catalyst and/or fresh 1,n-diaza compound in a repeated reaction. If required, a small amount of fresh catalyst and/or 1,n-diaza compound than that originally employed is added to maintain the full activity. If required, a portion of the mother liquor produced is separated off in order to remove by-products. In order to remove the salts, the reaction mixture can also be thoroughly stirred, preferably at an elevated temperature (85° to 95° C.,) with the amount of water required to dissolve the salts. After phase separation, the organic layer is worked up further, for example by steam distillation or by stripping off the constituents which are more readily volatile than the 4-nitrodiphenylamine.

If the 1,n-diaza compound employed is not recycled by reusing the mother liquor produced in the crystallization, the diaza compound can be recovered in most cases by customary methods. For example, distillative or extractive processes, if appropriate via the stage of salt formation, are suitable for this purpose.

By means of the process according to the invention, 4-nitrodiphenylamines can be prepared in outstanding yields and high purities. Virtually no formation of by-products occurs in the process according to the invention, so that no ecological problems arise. The 1,n-diaza compounds employed according to the invention have a pronounced accelerating effect on the reaction, thereby avoiding the disadvantage of long reaction times, and thus affecting the cost efficiency of the process. In addition, neutralizing agents which are cheaper than potassium carbonate can be used in the process according to the invention without the reaction being inhibited and the yields of 4-nitrodiphenylamine being reduced.

The yields of 4-nitrodiphenylamines achieved by means of the process according to the invention are particularly surprising in view of J. Org. Chem. 32, 2502, 2503, which describes the use of p-nitrobromobenzene as the halogen component in an Ullmann ether synthesis. From this reference it can be seen that in the copper-catalyzed substitution reaction described therein the yield of the substitution product is drastically decreased by the addition of 2,2'-dipyridine, that is to say a cyclic diaza compound.

The 4-nitrodiphenylamines prepared by the process according to the invention can readily be reduced by known processes to give aminodiphenylamines, and are, as such, valuable, intermediate products for the preparation of, for example, dyestuffs or stabilizers for rubber (see U.S. Pat. No. 3,163,616).

The examples which follow are intended to illustrate the process according to the invention, without, however, limiting it to these examples.

EXAMPLES 1 TO 5

Examples 1 to 5 of Table 1 below are comparative examples using sodium carbonate as the neutralizing agent.

The comparative examples show that no useful results are obtained when the complex-former described in U.S. Pat. No. 3,121,736 is employed and sodium carbonate is used instead of potassium carbonate.

TABLE 1

| Example No. | Co-catalyst | Reaction time hours | Weight ratio[a] | | |
|---|---|---|---|---|---|
| | | | Nitrobenzene: | 4-Nitrochlorobenzene: | 4-Nitrodiphenylamine |
| 1 | Glycine | 15 | 1.8: | 82.7: | 15.4 |
| 2 | o-Hydroxybenzal-o-aminophenol | 15 | 42.7: | 0.1: | 57.3 |
| 3 | 1,2-Disalicylal-diaminopropane | 15 | 34.7: | 0.2: | 65.1 |
| 4 | Trisodium nitrilotriacetate | 15 | 1.0: | 65.7: | 33.3 |
| 5 | Tetrasodium ethylene- | 24 | 2.8: | 52.2: | 45.0 |

TABLE 1-continued

| Example No. | Co-catalyst | Reaction time hours | Weight ratio[a] Nitrobenzene: | 4-Nitrochlorobenzene: | 4-Nitrodi- phenylamine |
|---|---|---|---|---|---|
| | diaminotetraacetate | | | | |

[a]determined by high pressure liquid chromatography (HPLC)
Reaction of 78.7 g of 4-nitrochlorobenzene (0.5 mol) with 93 g of aniline (1 mol) in the presence of 38 g of light sodium carbonate (0.36 mol), 1 g of CuO and 2.5 mol % of co-catalyst (relative to 4-nitrochlorobenzene). Stirred apparatus with a mounted 30 cm packed column and a water separator, xylene as the water entrainer, reaction temperature 195° C.

EXAMPLE 6

(Comparative example)

93 g of aniline, 2 g of CuO and 60 ml of xylene are heated under reflux to 150° C. for 20 minutes in a water separator. 76.3 g of anhydrous sodium carbonate, 157.5 g of 4-nitrochlorobenzene and 93 g of aniline are then added. After 20 hours at 195°–198° C., 4.5 ml of water have formed. The reaction mixture is suspended in water, and all volatile constituents are expelled with steam. The crude nitrodiphenylamine is isolated by filtration, washed with water and dried.

91.5 g of 4-nitrodiphenylamine, purity (HPLC) 80.8%, yield 34.5% of theory, relative to p-nitrochlorobenzene employed.

EXAMPLE 7

93 g of aniline, 3.8 g of 1,8-diazabicyclo[5,4,0]undec-7-ene, 2 g of copper(II)oxide and 40 ml of xylene are heated together to 150° C. for 20 minutes in a water separator. 157.5 g of 4-nitrochlorobenzene, 93 g of aniline and 76 g of calcined sodium carbonate (light) are then added. After 12 hours at 193°–196° C., 10 ml of water have collected in the water separator. The weight ratio of nitrobenzene:4-nitrochlorobenzene:4-nitrodiphenylamine in the reaction mixture is 1.5:2.0:96.5. The reaction mixture is cooled to 95° C. and filtered, and the filter cake is washed with 100 ml of hot xylene. Water is added to the filtrate, and unreacted 4-nitrochlorobenzene and aniline are expelled with steam, the 4-nitrodiphenylamine being obtained as granules. It is isolated by filtration, washed with hot water and dried: 210 g of 4-nitrodiphenylamine, purity (HPLC) 91.3%, yield 89.6% of theory, relative to p-nitrochlorobenzene employed.

EXAMPLE 8

Example 8 was carried out analogously to Example 7, but with 100 g of potassium carbonate instead of sodium carbonate. Reaction time 7 hours, working-up as described in Example 7: 214 g of 4-nitrodiphenylamine, purity (HPLC) 92.6%, yield 92.6% of theory.

EXAMPLES 9 TO 16

Examples 9 to 16 are listed in Table 2 below.

TABLE 2

| Example No. | 1,n-Diaza compound | Reaction time [hours] | Neutralizing agent | Weight ratio of 4-nitrochlorobenzene: 4-nitrodiphenyl-amine in the reaction mixture | 4-Nitrodiphenylamine yield [% of theory] relative to 4-nitrochlorobenzene employed |
|---|---|---|---|---|---|
| 9 | 1,10-Phenanthroline | 10 | $Na_2CO_3$ | 0.5:95.5 | 90.8 |
| 10 | 2,2'-Bipyridine | 12 | $Na_2CO_3$ | 2.3:97.7 | 87.6 |
| 11 | 1,2-Dimethyl-1,4,5,6-tetrahydro-pyrimidine | 15 | $Na_2CO_3$ | 4.5:95.5 | 86.8 |
| 12 | 1,2-Dimethyl-imidazole | 15 | $Na_2CO_3$ | 0.9:99.1 | 80.9 |
| 13 | 1,8-Diaza-bicyclo-[5,4,0]undec-7-ene | 10 | $NaHCO_3$ | 1.3:98.7 | 85.6 |
| 14 | 4-Dimethylamino-pyrimidine | 12 | $Na_2CO_3$ | 0.4:99.6 | 84.4 |
| 15 | 2,2'-Bipyridine | 8 | $K_2CO_3$ | 1.5:98.5 | 88.5 |
| 16 | 1,2-Dimethyl-imidazole | 6 | $K_2CO_3$ | 3.5:96.5 | 85.2 |

186 g (2 mols) of aniline, 157.5 g (1 mol) of 4-nitrochlorobenzene, 2 g of CuO, 1.42 equivalents of neutralizing agent and 0.025 mol of 1,n-diaza compound; procedure and working-up as described in Example 7.

EXAMPLE 17

186 g of aniline, 60 ml of xylene, 4.5 g of 1,10-phenanthroline, 157.5 g of 4-nitrochlorobenzene, 2 g of CuO and 76.3 g of potassium carbonate are heated to 195° C. for 7 hours in a water separator. The reaction mixture is cooled to 96° C. After the precipitated salts have been separated off by filtration, the filter cake is thoroughly washed with 200 ml of hot xylene. The filtrate and the washing liquid are combined, and after the solution has been cooled to 0° C., 127 g of 4-nitrodiphenylamine of melting point 128°–130° C. crystallize out and are separated off by filtration. 93 g of aniline, 157.5 g of p-nitrochlorobenzene and 76.3 g of potassium carbonate are added to the mother liquor produced in this procedure, and the mixture is freed from excess xylene by distillation, and heated at 195° C. for 11 hours in a water separator. After the salts have again been filtered off, the filtrate is worked up by steam distillation, as described in Example 7. 277 g of 4-nitrodiphenylamine of melting point 107°–111° C. are obtained.

EXAMPLE 18

121 g of 3,5-xylidine, 30 ml of xylene, 2.2 g of 1,10-phenanthroline and 1 g of CuO are heated to 155° C. for 30 minutes in a water separator. After 78.7 g of 4-nitrochlorobenzene and 38.1 g of sodium carbonate have been added, the mixture is boiled for 7 hours at 193°–195° C. in the water separator, and 5.2 ml of water are formed during this process. The working-up is effected as described in Example 7. 110 g of 3,5-dimethyl-4′-nitrodiphenylamine of melting point 179°–181° C. are obtained.

EXAMPLE 19

Analogous to Example 18, but 107 g of p-toluidine are employed instead of 3,5-xylidine. The reaction time is 8 hours. 114 g of 4′-methyl-4-nitrodiphenylamine of melting point 120°–122° C. are obtained.

EXAMPLE 20

Analogous to Example 18, but 107 g of o-toluidine are employed instead of 3,5-xylidine. The reaction time is 12 hours. 107 g of crude 2′-methyl-4-nitrodiphenylamine are obtained as a residue in the steam distillation.

EXAMPLE 21

186 g of aniline, 30 ml of xylene, 4.5 g of 1,10-phenanthroline and 2 g of CuO are heated to 150°–155° C. for 20 minutes in a water separator. After 157.5 g of 4-nitrochlorobenzene and 76 g of sodium carbonate have been added, the reaction mixture is boiled in the water separator for 9 hours at 193°–195° C., 9.9 ml of water being produced. The ratio nitrobenzene:4-nitrochlorobenzene:4-nitrodiphenylamine is 2.8:2.7:94.5 parts by weight. After the mixture has been cooled to 110° C., it is filtered off from the salts, and the filter cake is washed with 50 ml of xylene at 90° C. The filtrate and washing liquid are combined, and are subjected to incipient distillation in vacuo (15 mbar, temperature of the heating bath: up to 130° C.). 160 ml of xylene are added to the distillation residue while the latter is still warm, and the mixture is cooled to 5° C. whilst stirring. The product which has crystallized out is filtered off rapidly, and the filter cake is washed with 50 ml of ice-cold xylene and dried: 181 g of finely crystalline 4-nitrodiphenylamine of melting point 122°–125° C. The resulting filtrate is freed from excess xylene by distillation, and is recycled after the addition of 206 g of aniline, 157.5 g of 4-nitrochlorobenzene and 76 g of sodium carbonate.

After 11 hours at 193°–195° C., 10.2 ml of water have formed. The 4-nitrochlorobenzene conversion is 97%. The isolation of the 4-nitrodiphenylamine is effected by crystallization, as described above. 177 g of crystalline 4-nitrodiphenylamine of melting point 119°–120° C. are obtained after the product has been dried.

After 4 g of sodium sulphide containing water of crystallisation have been added, the mother liquor is filtered and then extracted three times with dilute hydrochloric acid. The aqueous phases are combined, rendered alkaline, and extracted with dichloromethane. The extract obtained after removal of the solvent contains 1,10-phenanthroline.

EXAMPLE 22

1.7 g of CuCl$_2$.2 H$_2$O, in the form of a concentrated aqueous solution, are added to a hot solution of 3.9 g of 1,10-phenanthroline in 100 ml of water. After the solution has cooled, the green copper complex which has crystallized out is isolated by filtration, and dried over P$_4$O$_{10}$ unit its weight remains constant.

93 g of aniline, 3.5 g of the copper complex obtained as described above, 78.5 g of 4-nitrochlorobenzene and 38 g of calcined sodium carbonate are heated to 193°–196° C. in a water separator, after 30 ml of xylene have been added.

After 10 hours, 4.9 ml of water are separated off. The weight ratio of 4-nitrodiphenylamine:p-nitrochlorobenzene in the reaction mixture is 97.3:2.7.

What is claimed is:

1. In a process for the preparation of a 4-nitrodiphenylamine of the formula

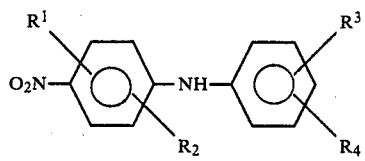

wherein
R$^1$, R$^2$, R$^3$ and R$^4$ are identical or different and independently represent hydrogen or an alkyl radical having 1 to 9 carbon atoms, by contacting a halogenonitrobenzene of the formula

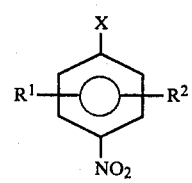

wherein
X represents chlorine or bromine and
R$^1$ and R$^2$ have the abovementioned meaning, with a primary aromatic amine of the formula

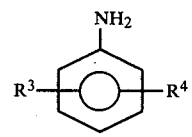

wherein
R$^3$ and R$^4$ have the abovementioned meaning, in the presence of a neutralizing agent and in the presence of copper or a copper compound, the improvement wherein the process is carried out in the presence of a cyclic, 1,n-diaza compound wherein n=3, 4 or 5, wherein the nitrogen atoms of said diaza compound do not carry any hydrogen and at least one nitrogen atom is constituent of a double and at least one nitrogen atom is a constituent of a ring, and the 1,n-diaza compound is incapable of forming an anion in an aqueous-alkaline solution.

2. A process according to claim 1, wherein said cyclic 1,n-diaza compound is an imidazole, imidazoline, pyrimidine, bicyclic amidine, triazine, phenantroline, dipyridine or biquinoline.

3. A process according to claim 1, wherein said 1,n-diaza compound is selected from the group consisting of 1-methyl-1-H-imidazole, 1-ethyl-1-H-imidazole, 1-butyl-1-H-imidazole, 1-phenyl-1-H-imidazole, 1-benzyl-1-H-imidazole, 1,2-dimethyl-1-H-imidazole, 1,2,4,5-tetramethyl-1-H-imidazole, 1-methyl-benzimidazole, 1-ethyl-2-methyl-benzimidazole, 1-butyl-4,5-dihydro-1-H-imidazole, 1-benzyl-2-methyl-4,5-dihydro-1-H-imidazole, 1-methyl-1,4,5,6-tetrahydrohydropyrimidine, 1,2-dimethyl-1,4,5,6-tetrahydropyrimidine, 1-ethyl-1,4,5,6-tetrahydropyrimidine, 1,5-diaza-bicyclo[4,3,0]non-5-ene, 1,5-diaza-bicyclo[4,4,0]dec-5-ene, 1,6-diaza-bicyclo[5,3,0]dec-6-ene, 1,8-diaza-bicyclo[5,4,0]undec-7-ene, 2,4,6-tri-(pyrid-2-yl)-1,3,5-triazine, 1,10-phenanthroline, 2,9-dimethyl-1,10-phenanthroline, 2,9-dimethyl-4,7-diphenyl-1,10-phenanthroline, 4,7-diphenyl-1,10-phenanthroline, 4,7-dimethyl-1,10-phenanthroline, 2,2'-bipyridine, 4,4'-dimethyl-2,2'-bipyridine, 4,4'-diethyl-2,2'-bipyridine, 4,4',6,6'-tetramethyl-2,2'-bipyridine, biquinoline, 4-dimethylainopyridine and 4-pyrrolidinoaminopyridine.

4. A process according to claim 1, wherein said 1,n-diaza compound is selected from the group consisting of 1-methyl-1-H-imidazole, 1,2-dimethyl-1-H-imidazole, 1,2-dimethyl-1,4,5,6-tetrahydropyrimidine, 1,8-diaza-bicyclo[5,4,0]undec-7-ene, 1,10-phenanthroline, 2,9-dimethyl-1,10-phenanthroline, 2,2'-bipyridine, biquinoline and 4-dimethylaminopyridine.

5. A process according to claim 1, wherein said 1,n-diaza compound is employed in an amount of 0.1 to 10% by weight, based upon the weight of halogenonitrobenzene employed.

6. A process according to claim 1, wherein said 1,n-diaza compound is employed in an amount of 0.5 to 5% by weight, based upon the weight of halogenonitrobenzene employed.

7. A process according to claim 1, wherein said 1,n-diaza compound is 1,8-diaza-bicyclo-[5,4,0]undec-7-ene.

8. A process according to claim 1, wherein said 1,n-diaza compound is 1,10-phenanthroline.

9. A process according to claim 1, wherein said 1,n-diaza compound is 2,2'-bipyridine.

10. A process according to claim 1, wherein said 1,n-diaza compound is 1,2-dimethyl-1,4,5,6-tetrahydropyrimidine.

11. A process according to claim 1, wherein said 1,n-diaza compound is 1,2-dimethylimidazole.

12. A process according to claim 1, wherein said 1,n-diaza compound is 4-methylaminopyridine.

* * * * *

UNITED STATES PATENT AND TRADEMARK OFFICE
CERTIFICATE OF CORRECTION

PATENT NO. : 4,404,400
DATED : Sep. 13, 1983
INVENTOR(S) : Klaus-Peter Heise and Karlfried Wedemeyer It is certified that error appears in the above–identified patent and that said Letters Patent are hereby corrected as shown below:

Column 12, line 49  Insert --bond-- after "double".

Signed and Sealed this

Third Day of April 1984

[SEAL]

Attest:

GERALD J. MOSSINGHOFF

Attesting Officer

Commissioner of Patents and Trademarks